United States Patent [19]

Huggins

[11] Patent Number: 4,530,364

[45] Date of Patent: Jul. 23, 1985

[54] COMPOSITION AND METHOD FOR EVALUATING SENSITIVITY TO METALS

[76] Inventor: Hal A. Huggins, 106 E. Cheyenne Rd., Colorado Springs, Colo. 80906

[21] Appl. No.: 489,061

[22] Filed: Apr. 27, 1983

[51] Int. Cl.$^3$ ................................................. A61B 5/00
[52] U.S. Cl. .................................. 128/670; 128/743; 604/304
[58] Field of Search ........ 128/743, 670, 668, 639–640, 128/672, 687, 736; 604/289–290, 304, 307

[56] References Cited

U.S. PATENT DOCUMENTS

| | | | |
|---|---|---|---|
| 3,212,495 | 10/1965 | Osbourn et al. | 604/307 X |
| 3,280,636 | 10/1966 | Tomberg | 128/670 X |
| 3,901,234 | 8/1975 | Yazawa | 604/307 |
| 4,158,359 | 6/1979 | Kurokawa et al. | 128/743 X |
| 4,450,844 | 5/1984 | Quisno | 128/743 |
| 4,466,431 | 8/1984 | Tharrat et al. | 604/304 X |

FOREIGN PATENT DOCUMENTS 0930668  7/1973  Canada ................................ 604/304

Primary Examiner—Lee S. Cohen
Assistant Examiner—Angela D. Sykes
Attorney, Agent, or Firm—Young & Martin

[57] ABSTRACT

A composition and method for testing and evaluating a person's sensitivity to metals, such as mercury and nickel includes an inorganic salt of that metal carried by a mixture of propylene glycol and deionized water. In the case of mercury, a base solution having 5% by weight of mercury chloride in deionized water is mixed with propylene glycol so that the resulting composition has between 0.1% and 2.5% by volume of the base solution. For nickel, between 4% and 7% by weight of nickel sulfate is mixed with a 50-50 mixture of propylene glycol and deionized water. The method includes the steps of measuring first values of the person's vital signs, applying the mercury or nickel composition to the skin by way of a bandage, measuring second values of the vital signs after a lapse of time, and comparing the first and second values.

6 Claims, No Drawings

COMPOSITION AND METHOD FOR EVALUATING SENSITIVITY TO METALS

BACKGROUND OF THE INVENTION

The present invention relates to compositions and a method for evaluating a person's sensitive reaction to the metallic substances of mercury and nickel. All people exhibit a reaction to substantial quantities of these metals, but some persons exhibit unusual sensitivity to small quantities of the metals. Indeed, these hypersensitive persons can exhibit extreme reactions to quantities of these metals that most persons apparently tolerate. Since these metals have been and continue to be used in the dental industry, the detection of those hypersensitive persons who are likely to have a sensitive reaction to the metals becomes important.

In the past, the diagnosis of some medical trauma included a measurement of mercury or nickel in the urine of the patient or in the blood of the patient. The tests were also used for evaluating a person's reactivity to these metals. Both of these tests, however, while providing valuable data, were not necessarily totally reliable. In the case of a blood test, only acute presence of the metal will be apparent. A urine test shows only that the body eliminates the metals; thus, a low mercury or nickel content in the urine may result from bodily retention of the metal rather than elimination of it. That is, a patient may retain a high amount of one of these metals and react in deleterious manner to the mercury or nickel even though it is not showing up in either his blood or urine. This is especially critical to the hypersensitive patient who may demonstrate acute reactions to even small quantities of these materials which quantities do not normally become apparent through either of these tests. In addition, neither of these tests help evaluate the potential dangers to the hypersensitive person who is exposed to low level, but long term doses of these materials such as occur when amalgams of mercury and nickel are used as dental fillings.

Further, some efforts have been directed, in the past, to testing reactions to mercury and nickel, utilizing mercury chloride and nickel sulfate mixed with petroleum jellies and applied to the skin of an individual. These techniques have not proved successful since the petroleum jellies have interferred with the absorption of the low level dosage of the toxic substance into the skin of the patient.

Accordingly, a need exists for a simple and convenient manner for testing an individual's sensitive reaction to metals, such as mercury and nickel. There is a further need for a composition and method that will allow medical personnel to distinquish the normally sensitive individual from the hypersensitive individual prior to that individual's exposure to a chronic, low level dosage of these metals.

SUMMARY OF THE INVENTION

It is therefore an object of the present invention to provide compositions that are novel and useful in evaluating a sensitive reaction of a person to various metals, such as mercury and nickel.

It is a further object of the present invention to provide a composition for determining the hypersensitivity of an individual to mercury and nickel and distinguishing these individuals from normally sensitive persons.

It is a still further object of the present invention to provide a composition for testing hypersensitivity to metallic materials which composition includes a small amount of the substance intimately mixed in a base carrier that provides an even absorption of the material into the skin of a patient.

Yet another object of the present invention is to provide a novel and useful method for testing the hypersensitivity of an individual to toxic metals without subjecting the individual to extreme dosages of those substances containing the metals.

The present invention contemplates a technique of applying a preferred composition to the skin of a patient in such a manner that permits a doctor or other medical personnel to evaluate the individual's sensitive reaction to that substance. This composition and method further allows the medical personnel to distinguish the hypersensitive individual from a normally sensitive person as an aid in diagnosing that person's sensitive reactions.

The preferred form of the compositions according to the present invention includes an intimate mixing of a small amount of an inorganic salt of the toxic metal with a base carrier that includes propylene glycol and deionized water. Since the human body is more reactive to mercury than to nickel, a smaller amount of mercury chloride is mixed with the base carrier and a greater amount of nickel sulfate is mixed with the base carrier in order to form a composition that may be applied to the skin of a patient. since it is important to distinguish between the normally sensitive person and the hypersensitive person, the preferred form of the present invention contemplates a composition that includes approximately 0.005% and 0.122% of mercury choloride by weight, and a composition containing approximately 4% to 6% nickel sulfate by weight.

The method according to the preferred embodiment of the present invention includes the steps of first measuring first values of selected vital signs of a patient. A composition containing a small percentage of an inorganic salt of the metal to be tested, a portion of propylene glycol and a portion of water is then placed on an adhesive bandage, and the bandage with the composition is placed on the skin of the individual, such as on the forearm, so that the composition is in contact with the skin. Second values of the vital signs are then measured after the lapse of a first interval of time, and the two measurements of vital signs are compared to calculate the change therebetween in order to determine whether or not the individual has reacted to the composition. Third values of the vital signs may be measured after a second interval of time, if desired. The calculated change in the vital signs enables an evaluation of the toxic reaction of the individual to the toxic metal. Preferably, the vital signs are measured approximately one to two hours after the bandage is applied, and the vital signs are again measured approximately one day, or 24 hours, after the bandage has been applied so that three distinct measurements are taken. In the preferred method, the heart rate, blood pressure and body temperature are each measured and compared.

These and other objects, advantages, and features of the present invention will become more readily appreciated and understood when taken together with the following detailed description, in which:

DETAILED DESCRIPTION OF THE PREFERRED EMBODIMENT

The present invention is directed to a composition and method used in testing hypersensitivity of an individual to toxic metals, such as mercury and nickel. Although every person is reactive in one degree or another to these sensitive materials, there is a class of persons who exhibit an extreme toxic reaction to even low level exposure to mercury and nickel. It should be appreciated that, as certain dosage levels, all persons react to these toxic substances while at minute levels, no apparent reaction is observed even in hypersensitive persons. In a range between these two extremes, it is important to distinguish the hypersensitive person, that is, one who reacts to low level dosages, from the normally sensitive individual.

The compositions according to the preferred embodiments of the present invention have been determined experimentally by placing differing amounts of an inorganic salt of mercury or an inorganic salt of nickel in a base carrier mixture. Since the human body is more sensitive or reactive to mercury than to nickel, different percentages of the metallic salt of mercury and nickel are utilized with the base carrier to distinguish the hypersensitive individual from the normally sensitive individual. Thus, the compositions for each of these metals will be described separately.

COMPOSITION FOR MERCURY

In order to develop a composition for determining the hypersensitivity of an individual to mercury, a 5% by weight solution of mercury chloride in deionized water was first prepared as a base solution. A first test solution was then prepared by mixing 1 milliliter of the base solution with 40 milliliters of propylene glycol to produce a 2.5% volumetric mixture of the base solution in propylene glycol.

Serial test solutions were then prepared from this base solution. A second solution was made by mixing 10 milliliters of the first test solution with 40 milliliters of propylene glycol. A third test solution was prepared by mixing 10 milliliters of the second test solution with 40 milliliters of propylene glycol. Finally, a fourth test solution was prepared by mixing 10 milliliters of the third test solution again with 40 milliliters of propylene glycol.

Each of these test solutions was then applied to test subjects by means of the patch test described below with respect to the method according to the preferred embodiment of this invention. The results of this test determine that none of the subjects reacted to the fourth test solution while the third solution did induce a reaction on approximately 5% or less of the subjects tested. The second solution induced a reaction on approximately 20–30% of the subjects; approximately 40–60% of the subjects had a reaction induced by the first test solution.

From these results, it was determined that the first test solution was a valuable aid in determining those people who had a tolerance to mercury, the second test solution was a value as an aid in determining those persons who had a sensitive reaction to mercury. Finally the third test solution proved valuable in detecting those persons who exhibited a hypersensitivity to mercury.

COMPOSITION FOR NICKEL

With respect to the test for sensitivity to nickel, a group of subjects were tested with different compositions containing nickel sulfate through the technique described in the method below. In this case, though, the base carrier was first prepared by mixing equal volumetric amounts of propylene glycol and deionized water. To this base carrier, varying amounts of nickel sulfate were mixed with the based carrier to form various weight percentage mixtures of nickel sulfate in the base carrier. From these tests, it was determined that, at levels of less than 4% by weight of nickel sulfate with the base carrier, approximately 5% or less of the subjects experienced a perceptable reaction to the presence of the nickel sulfate. Further, a majority of persons reacted to a composition that contained more than 7% nickel sulfate by weight and a moderate number of subjects, including the hypersensitive subjects reacted to a composition that contained between 4% and 7% nickel sulfate by weight with the base carrier. Specifically, it was found that approximately 20% reacted to a 5% composition, approximately 40% to the 6% composition, and approximately 45% to the 7% composition. Experimentally, the composition containing approximately 5% nickel sulfate, by weight, was most useful in inducing a reaction in those individuals who were candidates for toxic reaction to low levels of nickel.

It should be noted that the composition containing nickel sulfate also had a base carrier that was higher in water content that the composition containing mercury chloride. The use of a greater proportion of propylene glycol in the mercury base carrier is desirable since it aids in the absorption rate of the mercury into the subject's skin. This aid is not needed, though, where nickel is to be tested, but a higher proportion of propylene glycol could be used in the nickel sulfate base carrier.

METHOD FOR CONDUCTING THE TESTS

Noted above, the compositions containing mercury chloride and nickel sulfate were applied by means of a patch test developed for use with the compositions. This patch test, then, comprises the preferred embodiment of the present invention as it relates to the method of detecting sensitive reactions of the human body to toxic metals.

Accordingly, the method according to the preferred embodiment of the present invention includes the first step of measuring selected vital signs of the body, which vital signs are known to change when the body experiences a sensitive reaction. Preferably, the heart beat rate, the blood pressure, and the body temperature were first measured and the first values of each were recorded for each subject tested and, where a toxic test is to be undertaken, this should be the first step of the test. Next, a composition was placed on an adhesive bandage, which composition was formed of: (1) a small amount of an inorganic salt of the metal to be tested; (2) propylene glycol; and (3) deionized water. This composition, which is a gel-like substance, adheres nicely to the adhesive bandage having a center pad of gauze. This composition does not permit too rapid of an absorption of an inorganic salt while at the same time is self-adhering to the area of skin to which it is applied.

After the composition is placed on the bandage, the bandage is placed on the skin of the test subject, so that the composition is in contact with the skin. The bandage may be conveniently placed on the forearm of the subject. After a first interval of time has elapsed from the placing of the bandage on the individual, the vital signs that were originally measured are again measured to provide second values which are compared with the first values. Preferably, the first interval of time is a period of approximately 1 hour after the bandage has been placed upon the skin, although a period of 2 hours is readily appropriate. The second values obtained after the first interval of time may be compared with the first values obtained before the patch was applied with any difference in the measurements being used as an aid in evaluating whether or not the person has had an induced sensitive reaction. Preferably, the patch is left on the skin for approximately 24 hours, which is a second interval of time after which a third set of measurements are obtained. The third set of values are compared with the first and second values to again aid in evaluating any changes caused by the application of the composition to the skin of the patient.

Typically, a change in heart beat rate of ten beats per minute in either the second or third set of measurements over the first set of measurements is a good indicator of an induced reaction. Likewise, a change of ten points in the systolic or diastolic blood pressure over the initial set of readings may also indicate a sensitive reaction. It is also commonly observed that the body temperature of the patient may change approximately 0.5 degrees after the patch has been applied as an indicator of a sensitive reaction.

It should be understood, though, that the present invention contemplates the measurement of the vital signs at any convenient interval of time more than one hour after the patch has been applied. The time set forth above, though, is thought to be very pertinent in evaluating the patient's sensitive reaction to these metals.

While the present invention has been described with some degree of particularity, it should be appreciated that the present invention is defined by the following claims construed in light of the prior art so that modification or changes may be made to the embodiments of the present invention without departing from the inventive concepts comprised herein.

I claim:

1. The method of testing a person's sensitive reaction to metals such as mercury and nickel comprising the steps of:

measuring first values of selected vital signs of the person;

placing on an adhesive bandage a composition containing a small percentage of an inorganic salt of the metal for which the test is sought, a portion of propylene glycol, and a portion of water;

applying said bandage to the skin of the person so that the composition is in contact with the skin;

measuring second values of said selected vital signs after a first interval of time has elapsed after application of said bandage and composition; and comparing the first and second values of said vital signs to calculate the change therebetween.

2. The method according to claim 1 wherein said first interval is approximately 1 to 2 hours.

3. The method according to claim 1 wherein said first interval is approximately 24 hours.

4. The method according to claim 1 including the steps of measuring third values of said selected vital signs after a second interval of time has elapsed after application of said bandage and composition to the skin, and comparing said third values to said first and second values.

5. The method according to claim 4 wherein said first interval is approximately 1 hour and said second interval is approximately 24 hours.

6. The method according to claim 1 wherein the selected vital signs include heart beat rate, blood pressure and body temperature.

* * * * *